United States Patent
Wagner et al.

(10) Patent No.: US 9,410,875 B2
(45) Date of Patent: Aug. 9, 2016

(54) METHOD AND ARRANGEMENT FOR THE WEIGHTED MONITORING OF THE WEAR OF A PAIR OF HAND PLIERS USED FOR CRIMPING WORKPIECES

(75) Inventors: Thomas Wagner, Bermbach (DE); Sascha Zmiskol, Bamberg (DE); Andreas Marr, Bermbach (DE)

(73) Assignee: RENNSTEIG WERKZEUGE GMBH (DE)

( * ) Notice: Subject to any disclaimer, the term of this patent is extended or adjusted under 35 U.S.C. 154(b) by 179 days.

(21) Appl. No.: 14/123,029

(22) PCT Filed: May 26, 2012

(86) PCT No.: PCT/EP2012/059924
§ 371 (c)(1),
(2), (4) Date: Nov. 27, 2013

(87) PCT Pub. No.: WO2012/163866
PCT Pub. Date: Dec. 6, 2012

(65) Prior Publication Data
US 2014/0083149 A1    Mar. 27, 2014

(30) Foreign Application Priority Data

May 30, 2011   (DE) .......................... 10 2011 050 718

(51) Int. Cl.
*H01R 43/042*    (2006.01)
*G01N 3/56*    (2006.01)
(Continued)

(52) U.S. Cl.
CPC  *G01N 3/56* (2013.01); *B25B 27/10* (2013.01); *B25B 27/146* (2013.01); *H01R 43/042* (2013.01)

(58) Field of Classification Search
CPC ........ H01R 43/042; G01N 3/56; B25B 27/10; B25B 27/146

USPC ............ 72/14.8, 14.9, 15.1, 17.2, 19.8, 21.1, 72/21.4, 31.01, 31.1, 31.11, 31.12, 409.01, 72/409.14; 73/7; 29/751
See application file for complete search history.

(56) References Cited

U.S. PATENT DOCUMENTS 6,142,022 A     11/2000  Rueegg et al.
6,490,543 B1 *  12/2002  Jaw .................... G05B 19/4065
                                                  340/457.4
(Continued)

FOREIGN PATENT DOCUMENTS

DE    296 02 238    5/1996
DE    298 06 179    11/1998
(Continued)

OTHER PUBLICATIONS

International Search Report mailed Sep. 13, 2012, issued in connection with corresponding PCT Application No. PCT/EP2012/059924 with English language translation (5 pages total).
(Continued)

*Primary Examiner* — Peter DungBa Vo
*Assistant Examiner* — Joshua D Anderson
(74) *Attorney, Agent, or Firm* — Karin L. Williams; Mayer & Williams PC

(57) ABSTRACT

The invention relates to a method for monitoring the wear of a pair of hand pliers with which crimping elements can be pressed onto a workpiece and a particular degree of crimping $m_p$, to be obtained by actuating the pliers, set using a presetting device. An arrangement is described for carrying out this method, as is a pair of hand pliers implementing the method. The method includes: counting each actuation of the hand pliers and linking to the degree of crimping $m_p$ that has been set; reading out a wear prognosis value $V_t$, from a memory, for the degree of crimping that has been set; determining a total wear value V by adding up the wear prognosis value $V_t$ for each actuation; verifying whether the total wear value reaches or exceeds a defined threshold value $V_G$, and issuing a calibration request if necessary.

11 Claims, 3 Drawing Sheets

(51) Int. Cl.
  *B25B 27/10* (2006.01)
  *B25B 27/14* (2006.01)

(56) References Cited

U.S. PATENT DOCUMENTS

| | | | | |
|---|---|---|---|---|
| 6,615,103 | B2* | 9/2003 | Fujishima | B23Q 41/08 318/566 |
| 6,807,840 | B2 | 10/2004 | Wilhelm et al. | |
| 6,922,640 | B2* | 7/2005 | Vezzu | G07C 3/00 700/90 |
| 7,059,166 | B2* | 6/2006 | Bowles | B25B 27/10 29/237 |
| 7,143,007 | B2* | 11/2006 | Long | G05B 19/4065 702/183 |
| 8,613,210 | B2* | 12/2013 | Wagner | B25B 27/146 72/20.1 |
| 2008/0276678 | A1 | 11/2008 | Pacaud et al. | |

FOREIGN PATENT DOCUMENTS

| | | |
|---|---|---|
| DE | 298 15 312 | 1/1999 |
| DE | 200 12 887 | 12/2000 |
| DE | 100 60 165 | 6/2002 |
| DE | 10 2004 009 489 | 9/2005 |
| DE | 10 2009 026 470 | 12/2010 |
| EP | 0 419 129 | 3/1991 |
| EP | 2 025 475 | 2/2009 |
| WO | 2010/136346 | 12/2010 |

OTHER PUBLICATIONS

International Preliminary Report on Patentability mailed Jul. 22, 2013, issued in connection with corresponding PCT Application No. PCT/EP2012/059924 with English language translation (11 pages total).

* cited by examiner

METHOD AND ARRANGEMENT FOR THE WEIGHTED MONITORING OF THE WEAR OF A PAIR OF HAND PLIERS USED FOR CRIMPING WORKPIECES

FIELD OF THE INVENTION

The present invention relates to a method for monitoring the wear of a pair of hand pliers for crimping workpieces and to an arrangement suitable for this. The invention also relates to a pair of hand pliers in which the wear is monitored. In particular, hand pliers are concerned in which crimping elements are pressed onto a workpiece and a degree of crimping to be obtained by actuating the crimping pliers can be set using a presetting device. The invention is specifically adapted for use with crimping pliers whose crimping capacity can be set.

BACKGROUND OF THE INVENTION

It is known to monitor wear in crimping machines. To assess the wear of a crimping tool in EP 0 419 129 B1, for example, dimensional changes in the crimping press are detected with the aid of an extensometer and compared to a range of acceptable crimping forces for a specific crimping level. Where a specific crimping force is no longer achieved as a result of wear, an adjustment signal is output which prompts a readjustment of the crimp contacts.

A readjustment signal for crimping pliers is known from DE 10 2004 009 489 A1 in which the crimping punch that acts on the crimp contacts is brought into the crimping position by a swivel piston guided in a curved body. A selected presetting of the crimping pliers is indicated by an electronic display. However, if the crimp stamp or the curved body become worn, then the display of the value for the presetting will contain an error.

DE 296 02 238 U1 shows a testing device for testing crimping devices or parts supporting the press jaws thereof. The crimping device or a part thereof must be placed in a specific position in the testing device. During the testing procedure empty crimping is carried out, whereby after the crimping force is applied the gap width between two opposing end faces of adjoining crimping jaws is measured. The gap width is displayed to the operator in order for the latter to decide whether the crimping device can continue to be used or not. This solution is suitable only for crimping devices in which the crimping jaws essentially impact one another when the crimping device is actuated or with which only a single degree of crimping is realized.

The document DE 200 12 887 U1 displays a device for testing the wear on crimping pliers. This device comprises a test element that includes an indicator which is to be arranged between the end faces of the crimping jaws when an object is crimped. The indicator is compressed to less than a predetermined comparatively small gap width. This solution is also only suitable for crimping pliers in which the crimping jaws essentially impact one another when the crimping device is actuated or with which only a single degree of crimping can be realized.

EP 2 025 475 A2 describes a pressing device for joining workpieces and a method for performing a technical diagnosis of the pressing device. Information representing the number of strokes and at least one piece of operating information per operating second of the drive are continually stored in an information memory of the device. Operating information of the drive, for example, in the form of the power input of the electric motor or pressure measurement data of an electrohydraulic drive and/or the force measurement data in the area of the pressing tool are stored as operating information. Additional stored data may include the temperature and/or date or period of operation of the drive. Based on the stored information, it is possible to subsequently analyze the operation of the pressing device in order, for example, to determine gradually occurring wear, so that, if necessary, prognoses can be made on the number of pressing operations that can still be successfully executed.

A pair of crimping pliers is known from US 2008/0276678 A1 which comprise a force sensor, a position sensor, a data processing unit and a display. The quality of the crimping result can be indicated on the display by colored LEDs (red, green).

A method and a device for monitoring the wear on a pair of hand pliers is known from DE 10 2009 026 470 A1, in which the degree of crimping is adjustable by means of a presetting device. In this device a reference setting of the presetting device is first detected in which the crimping elements are not yet subject to wear. Measurement of the wear status of the presetting device is repeated after being activated a specific number of times. Wear cannot be detected and precise standard crimping cannot be assured, if the wear measurement is not carried out by the user in the predetermined intervals.

SUMMARY OF THE INVENTION

The object of the present invention consists in monitoring the use-related wear of a pair of hand pliers and, upon projected attainment of a defined wear threshold, in forcing a calibration. At the same time the interval between forced calibration processes should be kept as infrequent as possible to avoid importuning the user too frequently with this process.

The object is achieved by a method having the features of claim 1, by an arrangement for carrying out this method as recited in claim 8 and by a pair of hand pliers as recited in claim 9.

A method according to the invention serves to continually monitor the wear of a pair of hand pliers. This involves the type of hand pliers in which the crimping elements can be pressed onto a workpiece and a particular desired degree of crimping can be set using a presetting device.

The method is based on the fundamental idea that the actual wear is dependent on the degree of crimping set during pressing. That is to say, when using a small workpiece (for example, a small crimping contact) the degree of crimping is small, a relatively low force being required for crimping, resulting in minimal load and minimal wear, as compared to the crimping of large workpieces with a high degree of crimping in which greater wear occurs as a result of greater forces.

The advantages of the invention are seen particularly in the fact that useful and application-specific calibration intervals for a pair of hand pliers are defined and monitored, and calibration is actively requested. In this way time-consuming, unnecessary calibration processes can be avoided on the one hand, while on the other hand a prompt request for calibration is made in the event of increased use and the resultant anticipated wear values. This makes it possible to consistently obtain a correct crimping result. In some cases, the hand pliers may be locked after reaching a theoretical wear value and further use is prevented until a recalibration is performed.

In the method each actuation of the hand pliers is first counted and linked to a degree of crimping that has been set. Various wear prognosis values are stored in a memory for different degrees of crimping, which are ascertained empirically, for example, by the manufacturer. In a second step, the associated wear prognosis value for each completed actuation is read out from a memory, and a total wear value is determined by adding up the wear prognosis values of multiple actuations and is stored in the memory.

The wear prognosis values are preferably determined by testing or are based on experience. Mathematical functions may also be stored for calculating the expected wear prognosis values.

Moreover, in preferred embodiments of the method, the number of actuations for each degree of crimping may also be stored. For this purpose, a separate enumerator may be provided for each class of degrees of crimping.

If the total wear value reaches a defined threshold, a request for calibration of the hand pliers is issued. The request is issued preferably via a display present on the hand pliers, but may also be variously issued, for example by an acoustic signal or a mechanical lock. The threshold value is defined, for example, by a standard to be observed or is predefined by the manufacturer.

The calibration itself may be accomplished in the known manner described, for example, in DE 10 2009 026 470 A1.

During calibration, actual wear is determined which is also stored in the memory. This should also preferably be representable in the display, for example, as a percentage in conjunction with a remaining use display. The total wear value ascertained theoretically from the wear prognosis values is reset. The correction value itself used in the calibration process is likewise preferably added up in a separate enumerator.

During further operation of the hand pliers, summation occurs preferably precisely in a cyclical manner up to the first calibration. Reaching a threshold value of the total wear again is followed once again by a request for calibration.

If the end of the overall service life is reached, i.e. the maximum amount of wear has occurred, the pliers should no longer be used. To that end a warning may be output in the display or in a preferred embodiment, for example, a mechanical locking of the hand pliers may be triggered, as a result of which no further actuation is possible.

According to another preferred embodiment, a sensor may be used to detect whether in fact a relevant pressing force was generated during actuation of the pliers. In this way, empty actuations are masked that are captured by a simple enumerator, but in conjunction with which no wear appears on the pliers. The accuracy of the wear prognosis is further enhanced in this way. A sensor of this type can be integrated as a force sensor in the handles or in other structural elements situated in the flux of force of the hand pliers or directly to or in the crimping elements.

According to a modified embodiment, the difference between the real wear ascertained during calibration and the total theoretical wear can be taken into account for an adjusted future prognosis. If the real wear during the first forced calibration is, for example, just 50% of the theoretically determined wear value, the stored wear prognosis values in future periods may be impacted with a factor <1. However, the threshold value should always be selected so that the allowable tolerances for the crimping elements of the pliers are never exceeded before the next calibration is forced. In addition, the calibration cycles may of course also be adapted to the respective wear status of the pliers.

An arrangement according to the invention for monitoring the wear of a pair of pliers comprises a memory. Stored in the memory are theoretical wear prognosis values for different adjustable degrees of crimping. Also provided in the memory are memory locations for storing the monitored data of the method. The monitoring data preferably include a enumerator for each degree of crimping, a total enumerator of all pressings, a enumerator for the calibration process and of the actually determined wear during the last calibration process. The arrangement according to the invention also comprises a device for detecting the actuation of the hand pliers. This may be a limit switch, for example, that is arranged at a stop between the handles of the hand pliers. The wear prognosis values are added together by a computing unit formed preferably by an integrated microcontroller system. The device also comprises a display unit for displaying different data of the wear control.

A known pair of pliers for crimping workpieces may be upgraded in a simple manner by means of the method according to the invention and by means of the arrangement according to the invention. If, for example, the pliers already comprise a display, an actuation enumerator and a microprocessor, it is possible via a factory installed software update to integrate the automatic monitoring functionality into the hand pliers.

Further advantages, details and refinements of the invention will become apparent from the following description of a preferred embodiment of the hand pliers according to the invention, with reference to the drawing.

DETAILED DESCRIPTION

Figure 1:
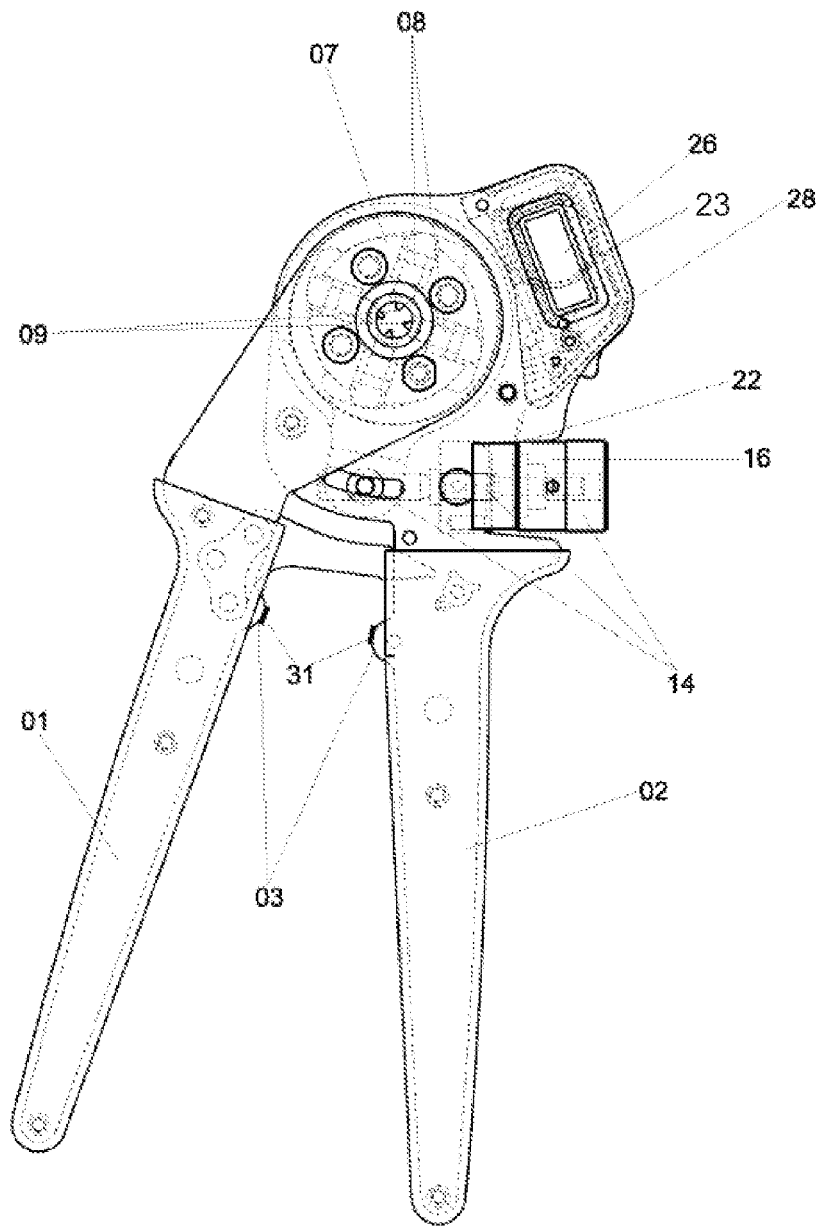
FIG. 1 shows a view of a pair of hand pliers fitted with an arrangement according to the invention with edges depicted as hidden.

FIG. 1 shows a preferred embodiment of hand pliers fitted with the arrangement according to the invention, namely crimping pliers. Hidden body edges are depicted in this view by dashed lines. The hand pliers are manually actuated crimping pliers for crimping electrical connecting elements, whose functionality is described in detail in DE 10 2009 026 470 A1, which is incorporated in the disclosure content of this application.

The crimping pliers comprise a first hand lever 01 and a second hand lever 02, which are pivotable relative to one another. When the crimping pliers are closed the two hand levers 01, 02 impact one another against stop surfaces 03.

Four crimping elements 08 formed by notch elements are arranged for radial movement in a guide body 07. The four crimping elements 08 together form a crimp die and each includes an anvil surface 09 provided for pressing a notch in the electrical connecting element to be crimped. By actuating the crimping pliers, the four crimping elements 08 are moved toward one another. An electrical connecting element to be crimped, which is disposed between the anvil surface 09 of the crimping elements 08 is then crimped, whereby the anvil surface 09 of the crimping elements 08 presses notches into the electrical connecting element.

The degree of crimping, i.e. the distance between the anvil surfaces 09 of the pressing elements 08 achieved when closing the crimping pliers completely can be set by means of a presetting device 14. Adjustment of the degree of crimping using the presetting device 14 serves to adapt the hand pliers to electrical connecting elements of various sizes, and also to allow for compensation of wear to the hand pliers, in particular, wear to the anvil surfaces 09 of the pressing elements 08 and, if necessary, the cam stop surfaces.

The position of the presetting device 14 can be measured with a rotary encoder 22 that is electrically connected to a microcontroller system. The microcontroller system in turn is electrically connected to a digital display 26 on which information may be displayed alphanumerically.

In the embodiment of the hand pliers according to the invention, the adjustable degree of crimping is between 0.65 mm and 3 mm, for example.

The hand pliers may also be designed for degrees of crimping on different scales, for example, in the sub-millimeter or centimeter range.

Once the hand pliers are produced, they must undergo a calibration process prior to first use, as described in DE 10 2009 026 470 A1. For the calibration it is necessary to use a calibration mandrel of a diameter (not shown) known to the system which, in the embodiment shown, has a diameter of, for example, 2 mm. By adopting the degree of crimping calibrated with the calibration mandrel, the hand pliers become operational At this point, the hand pliers may be adapted to crimping degrees of varying scale by adjusting the presetting device 14, the instantaneous degree of crimping being displayed in the display 26.

The method according to the invention is implemented in the microcontroller system. A limit switch 31 connected to the microcontroller system 23 is provided at the stop surfaces 03 of the handles 01, 02 for counting the actuations. The limit switch may also be positioned elsewhere, for example, proximate the rotary encoder. The limit switch may also be actuated as the pliers are closed by a ratchet provided.

At this point, a theoretical wear prognosis value is added up with each activation of the hand pliers, as described in the following manner. Each wear prognosis value to be used is read out from a memory in response to a set degree of crimping (to be described in greater detail with reference to FIG. 3). When a particular threshold value of the wear prognosis value (for example, 0.01 mm) is exceeded, the user is then presented a request to calibrate (CAL) in display 26. At this point it is also possible to block the pliers in order to permit further use only after calibration has been performed.

For the calibration process, the hand pliers must be closed and the degree of crimping must be set with the aid of the presetting device 14 in such a way that the calibration mandrel slides with no play between the anvil surfaces 09 of the crimping elements 08. If wear has in fact occurred, the setting of the presetting device 14 now selected will deviate from the setting of the presetting device 14 during the previous calibration process. This deviation can be measured by the microcontroller system 23 based on a difference between electrical impulses of the rotary encoder 22. Since the link between the adjustment of the presetting device 14 and the change of degree of crimping is known, this difference in impulses of the rotary encoder 22 can be converted to a degree of crimping for the actual wear of the anvil surfaces 09. This actual degree of wear is stored in the microcontroller system 23 and may be represented in the display 26 either directly or converted to a remaining service life. In a new pair of pliers, for example, "100%" is displayed, then backwards in response to the wear in 1% increments, i.e. 99%, 98%, etc.

The totaled wear prognosis value is reset after each calibration process. Stored in the microcontroller system are the number of calibrations, the number of crimpings overall and the number of crimpings for each degree of crimping. Based on these data, the manufacturer is able to further approximate the theoretical wear prognosis values for subsequent software versions.

If the particular actual degree of wear is more than a preset allowable degree of wear, the microcontroller system 23 displays an error message "E1" in the display 26. The user of the hand pliers knows at this point that the anvil surfaces 09 of the crimping elements 08 are worn to the point that the hand pliers may no longer to be used.

In the embodiment of the hand pliers shown, the preset allowable degree of wear is, for example, 0.1 mm. The user would still be able to set a degree of crimping to be achieved of, for example, 1.5 or 2.0 mm with the aid of the presetting device 14, and to precisely calibrate the display of the degree of crimping to this. However, the user is prevented from doing so by the error message and/or by a mechanical blocking of the pliers. This prevents the user from performing crimping operations in which the anvil surfaces 09 of the crimping elements 08 are worn beyond that which is permissible, for example, when the tips of the anvil surfaces 09 are flattened.

If the second button 28 is actuated for a predetermined period of time, then multiple values are displayed successively in the display 26. For example, a serial number of the hand pliers is initially displayed. The actual wear value determined during the last performed calibration or remaining service life in % is then displayed as the next value. Following that can be a display of the degree of crimping that was calculated during the first calibration of the hand pliers for the reference setting of the presetting device 14. This involves therefore the smallest adjustable degree of crimping that could be set for the hand pliers in the unworn state. Finally, the number of calibrations performed since the hand pliers were manufactured could be displayed. After each calibration a enumerator is increased in the microcontroller system 23, which represents the number of calibrations performed to that point.

Figure 2:
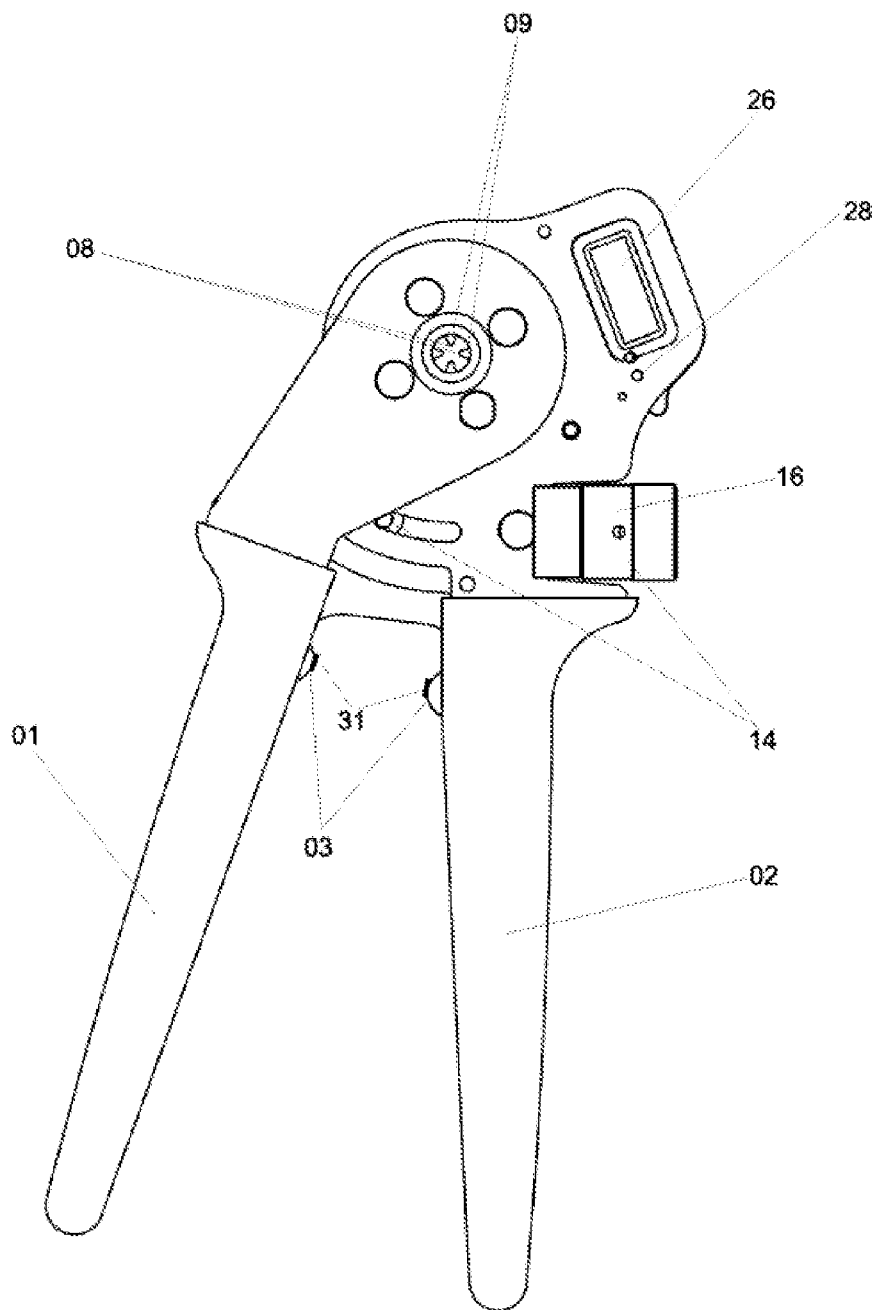
FIG. 2 shows another view of the hand pliers depicted in FIG. 1 with a presetting device set at a lower stop.

FIG. 2 shows hand pliers depicted in FIG. 1 in a view in which the hidden edges are not shown. In contrast to the state of the hand pliers shown in FIG. 1, the presetting device 14 is located at the lower stop of the former.

Figure 3:
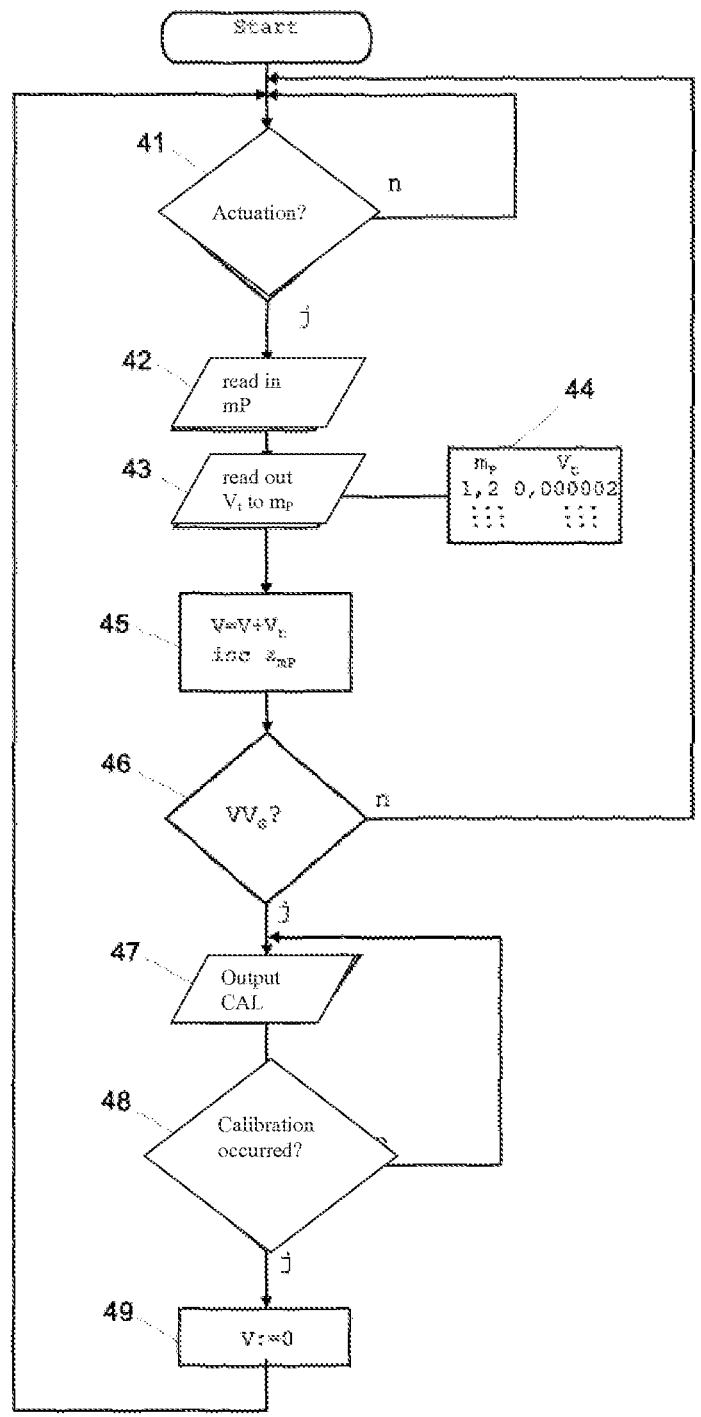
FIG. 3 shows a program sequence of a preferred embodiment of the method according to the invention.

FIG. 3 shows an exemplary flow chart of the method according to the invention that is implemented in the microcontroller system 23.

The method starts preferably by setting the degree of crimping on the hand pliers. In a method step 41, actuation of the pliers preferably by means of the limit switch 31 is queried and detected. In a second step 42 a preset degree of crimping $m_P$ is read in from the presetting device 14 preferably by means of the rotary encoder 22. However, it is equally possible for the degree of crimping $m_P$ to be stored directly in the microcontroller system 23 when set by the presetting device 14 and to be read in from there. In step 43 a wear prognosis value $V_t$ for the preset degree of crimping is read from a memory 44. Also deposited in memory 44 are numerous wear prognosis values $V_t$ for the typically associated degrees of crimping $m_P$. It is equally possible for wear prognosis values for intermediate values of the degrees of crimping to be calculated by the microcontroller. The stored wear prognosis values were determined by the manufacturer, for example, in a fatigue test for different degrees of crimping $m_P$. In one exemplary case, a defined wear of 0.1 mm with 50,000 actuations was verified for a test wire having a diameter of 2.67 mm at a preset degree of crimping of 1.2 mm. This corresponds to a theoretical wear prognosis value $V_t$ of 2 nm per pressing. Advantageously, 24 degrees of crimping $m_P$ (classes)) are provided in the setting range of 0.6 mm to 3.2 mm.

In step 45 the wear value is added to an overall wear V and added at least to the enumerator $Z_{mP}$ of the associated degree of crimping.

In a next step 46 it is queried whether the total wear V ascertained reaches or exceeds a defined threshold $V_G$ (for example, 0.01 mm). If this is the case, an issuance 47 of a request for calibration occurs on the display 26. For the operator, this is an indication not to use the pliers until after calibration. If necessary, a mechanical lock may also ensure that a calibration must first be performed before the hand pliers can be actuated again. If a query 48 reveals that calibration has occurred, the total wear V is reset. During calibration, the actual wear is ascertained in a known manner. The latter is stored in memory and may be represented by the display in % of remaining service life.

LIST OF REFERENCE NUMERALS

01—first hand lever
02—second hand lever
03—stop surfaces
07—guide body
08—crimping element
09—anvil surface
14—presetting device
16—knurled screw
22—rotary encoder
23—microcontroller
26—digital display
28—second button
31—limit switch
41—43 method steps
44—memory
45-49 method steps

What is claimed is:

1. An arrangement for monitoring the wear of a pair of hand pliers having crimping elements that can be pressed onto a workpiece, the arrangement, comprising:
    a data memory in which theoretical wear prognosis values Vt corresponding to dimensional changes of the crimping elements due to wear based on each actuation of the hand pliers at different degrees of crimping are stored, wherein the degree of crimping is defined by the distance between the crimping elements during actuation;
    means for detecting the actuation of the hand pliers and the degree of crimping;
    a computing unit configured to add up the associated theoretical wear prognosis values for each detected actuation and degree of crimping to arrive at a cumulative total wear value V; and
    a display unit configured to display a message if when the cumulative total wear value V reaches a defined threshold VG.

2. An arrangement for monitoring the wear of a pair of hand pliers according to claim 1,
    wherein said means for detecting actuation of the hand pliers is dependent on the triggering of a limit switch or on the detection of a predefined actuation force on the hand pliers ascertained by a force sensor.

3. An arrangement for monitoring the wear of a pair of hand pliers according to claim 2,
    wherein the wear prognosis value is determined by adding up force-dependent wear prognosis values that are stored in a memory.

4. An arrangement for monitoring the wear of a pair of hand pliers according to claim 1
    wherein the crimping elements can be pressed onto a workpiece on which a predetermined degree of crimping mP to be obtained by actuating the crimping pliers can be set using a presetting device.

5. An arrangement for monitoring the wear of a pair of hand pliers according to claim 1,
    wherein a message on the wear status is output and/or a lock signal is generated when the total wear value V exceeds the defined threshold $V_G$.

6. Hand pliers having crimping elements that can be pressed onto a workpiece, said hand pliers comprising an arrangement for determining wear of the hand pliers comprising:
    a data memory in which theoretical wear prognosis values Vt corresponding to dimensional changes of the crimping elements due to wear based on each actuation of the hand pliers at different degrees of crimping are stored, wherein the degree of crimping is defined by the distance between the crimping elements during actuation;
    means for detecting the actuation of the hand pliers and the degree of crimping of the hand pliers;
    a computing unit configured to add up the associated theoretical wear prognosis values for each detected actuation and degree of crimping to arrive at a cumulative total wear value V; and
    a display unit configured to display a message if when the cumulative total wear value V reaches a defined threshold VG.

7. The hand pliers according to claim 6, wherein the means for detecting the actuation comprises a limit switch or a force sensor.

8. The arrangement according to claim 7, wherein the data memory and the computing unit are formed by a microcontroller system and the display unit is a digital display that is coupled to the microcontroller system.

9. The hand pliers according to claim 6, wherein the data memory and the computing unit are formed by a microcontroller system and the display unit is a digital display that is coupled to the microcontroller system.

10. The hand pliers according to claim 6, wherein a preset degree of crimping $m_P$, the total wear V determined, or a remaining service life may be selectively represented in the display unit.

11. Hand pliers having crimping elements that can be pressed onto a workpiece, said hand pliers comprising an arrangement for determining wear of the hand pliers according to claim 9.

* * * * *